US00PP17159P2

(12) United States Plant Patent
Austin

(10) Patent No.: US PP17,159 P2
(45) Date of Patent: Oct. 17, 2006

(54) SHRUB ROSE PLANT NAMED 'AUSJAMESON'

(50) Latin Name: *Rosa hybrida*
Varietal Denomination: AUSjameson

(75) Inventor: David C. H. Austin, Wolverhampton (GB)

(73) Assignee: David Austin Roses Ltd., Wolverhampton (GB)

( * ) Notice: Subject to any disclaimer, the term of this patent is extended or adjusted under 35 U.S.C. 154(b) by 0 days.

(21) Appl. No.: 11/048,987

(22) Filed: Feb. 1, 2005

(51) Int. Cl.
*A01H 5/00* (2006.01)

(52) U.S. Cl. ..... Plt./102

(58) Field of Classification Search ..... Plt./102, Plt./104, 105, 107, 130, 132, 134, 135
See application file for complete search history.

*Primary Examiner*—Howard J. Locker
(74) *Attorney, Agent, or Firm*—Klarquist Sparkman LLP

(57) ABSTRACT

Shrub rose plant suitable for cut flower production in greenhouse conditions, substantially as herein shown and described, characterized particularly by its upright growth, apricot, rosette-shaped blooms and light Tea fragrance.

1 Drawing Sheet

Genus and species: *Rosa hybrida.*
Variety denomination: 'AUSjameson'.

ORIGIN OF THE INVENTION

The present invention relates to a new and distinct variety of a shrub rose plant named 'AUSjameson' which was originated by me by crossing an unnamed, unpatented seedling with an unnamed, unpatented seedling.

BACKGROUND OF THE INVENTION

The primary objective of this breeding was to produce a plant suitable for year round cut flower production under standard greenhouse conditions having apricot blooms which are fragrant and have long vase life, produced on strong, upright stems.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Apricot, rosette-shaped blooms.
2. Upright growth.
3. Light Tea fragrance.
4. Suitable for cut flower production under greenhouse conditions.

Asexual reproduction of this new variety by budding, as performed at Albrighton, England, shows that the foregoing and all other characteristics and distinctions come true to form and are established and transmitted through succeeding propagations.

COMPARISON WITH PARENTS

'AUSjameson' has apricot rosette-shaped blooms which differ from the large, white, globular blooms of the seed parent and the soft yellow blooms of the pollen parent and its growth is less compact than that of its pollen parent.

COMPARISON WITH SIMILAR VARIETY

'AUSsaucer' (U.S. Plant Pat. No. 8,680) has an Old Rose fragrance and more petals than 'AUSjameson'.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—Unnamed Seedling (Unpatented).
*Pollen parent.*—Unnamed Seedling. (Unpatented).

FLOWER

Observations made from plants commencing at two years of age grown in a greenhouse environment at Albrighton, England.

Blooming habit: Continuous.

Bud:
*Size.*—About 2 cm long and 1.3 cm in diameter when the petals start to unfurl.
*Form.*—The bud form is pointed ovoid.
*Color.*—When sepals first divide, bud color is Orange Group 28C. When half blown, the upper sides of the petals are Orange Group 29C; and the lower sides of the petals are Red Group 36C.
*Sepals.*—Color: Upper surface: Green Group 138B. Lower surface: Green Group 137C. Length: 2.6 cm. Width: 1.1 cm. Shape: Subulate. Surface texture: Upper surface: Smooth. Lower surface: Pubescent.

There are three lightly appendaged sepals. There are two unappendaged sepals with canescent edges.

*Receptacle.*—Color: Green Group 143C. Shape: Campanulate. Size: Medium, about 1 cm long×1 cm wide. Surface: Smooth.

*Peduncle.*—Length: Medium, averaging about 6 cm. Surface: Smooth. Color: Yellow-Green Group 144A. Strength: Strong.

Bloom:

*Size.*—Large. Average open diameter is about 10.2 cm.

*Borne.*—In corymb-shaped clusters of two to three blooms. For cut flower production buds may be nipped out to leave a single bloom.

*Flowering stems.*—Strength: Strong. Average length is about 55 cm with a diameter of 5 mm.

*Form.*—When first open: Cupped. Permanence: Outer petal edges curl slightly.

*Petalage.*—Number of petals under normal conditions: 92.

*Color.*—The upper sides of the petals are Yellow-Orange Group 22C. The reverse sides of the petals are Yellow-Orange Group 20D. The bases of the petals are Yellow Group 12B. The major color on the upper sides is Yellow-Orange Group 22C.

*Variegations.*—None.

*Discloration.*—The general tonality at the end of the first day: Yellow-Orange Group 22C. At the end of the third day: Orange Group 27C.

*Fragrance.*—Slight, Tea.

Petals:

*Texture.*—Satiny.

*Size.*—Width: 3.8 cm. Length: 4.5 cm.

*Surface.*—Smooth.

*Shape.*—Round. Margin: Entire and reflexing. Apex Shape: Cuspidate. Base Shape: Pointed. Form: Incurved with tips slightly recurved.

*Arrangement.*—Quartered.

*Petaloids.*—Number: 6. Color: Yellow Group 13C.

*Persistence.*—Petals hang on and dry.

*Lastingness.*—On the plant: Long (about 6–8 days). As a cut flower: Long (about 6–8 days).

Reproductive parts:

*Stamens.*—Number: 70. Length: 10 mm. Anthers: Length: 2 mm. Color: Yellow-Orange Group 17A. Arrangement: Mixed with petaloids. Filaments: Color: Yellow Group 13A. Length: 8 mm. Pollen: Color: Yellow-Orange Group 17A.

*Pistils.*—Number: 30. Length: 12 mm. Styles: Color: Green-White Group 157A. Length: 11 mm. Stigmas: Color: Yellow Group 11A. Length: 1 mm.

*Hips.*—None observed.

PLANT

*Form.*—Shrub.

*Growth.*—Vigorous, upright, bushy.

*Age at maturity.*—One and one-half years.

*Mature plant.*—Height: 1.1 m. Width: 0.75 m.

*Rootstock.*—*Rosa multiflora inermis* for the observed plants.

Foliage: Number of leaflets on normal mid-stem leaves: 5 or 7 including terminal leaflet.

*Size.*—Large. About 17.5 cm long×14 cm wide.

*Quantity.*—Normal. Average number leaves per flowering stem: 7.

*Color.*—New foliage: Upper side: Yellow-Green Group 146A. Lower side: Yellow-Green Group 146C with tint of Greyed-Red Group 178C. Old foliage: Upper side: Green Group 139A. Lower side: Green Group 138A.

Leaflets:

*Size.*—About 8 cm long×5 cm wide.

*Shape.*—Oval.

*Base shape.*—Obtuse.

*Apex shape.*—Cuspidate.

*Texture.*—Smooth, leathery. On Upper Surface: Matte on young and mature surfaces.

*Edge.*—Serrated.

*Serrations.*—Single.

*Petiole.*—Color: Yellow-Green Group 144B.

*Petiole rachis.*—Color: Yellow-Green Group 144B. Underside: With prickles.

*Stipules.*—Length: 1.7 cm.

*Auricles.*—Elongated awl-shaped.

*Disease resistance.*—Resistant to mildew, blackspot and rust in greenhouse average day temperature maintained at 17.5 degrees C.

*Pest resistance.*—Not tested.

*Vein color.*—Yellow-Green Group 145C.

*Venation pattern.*—Reticulate.

Wood:

*New wood.*—Color: Yellow-Green Group 144A. Bark: Smooth.

*Old wood.*—Color: Green Group 137C. Bark: Smooth.

*Internode distance.*—9 cm.

*Flowering stems.*—15–17.

Prickles:

*Quantity.*—On main canes from base: Ordinary, 16 per 5 cm stem length. On laterals from main canes: Ordinary, 13 per 30 cm per stem length.

*Form.*—Hooked downward.

*Length.*—8 mm.

*Color when young.*—Greyed-Yellow Group 160A with tint of red.

*Color when mature.*—Orange-Red Group N34B with Grey-Yellow Group 160C at base.

Small prickles:

*Quantity.*—On main stalks: None. On laterals: None:

Winter hardiness: Not tested.

I claim:

1. A new and distinct variety of rose plant of the shrub class suitable for cut flower production in greenhouse conditions, substantially as herein shown and described, characterized particularly by its upright growth, apricot, rosette-shaped blooms and light Tea fragrance.

* * * * *

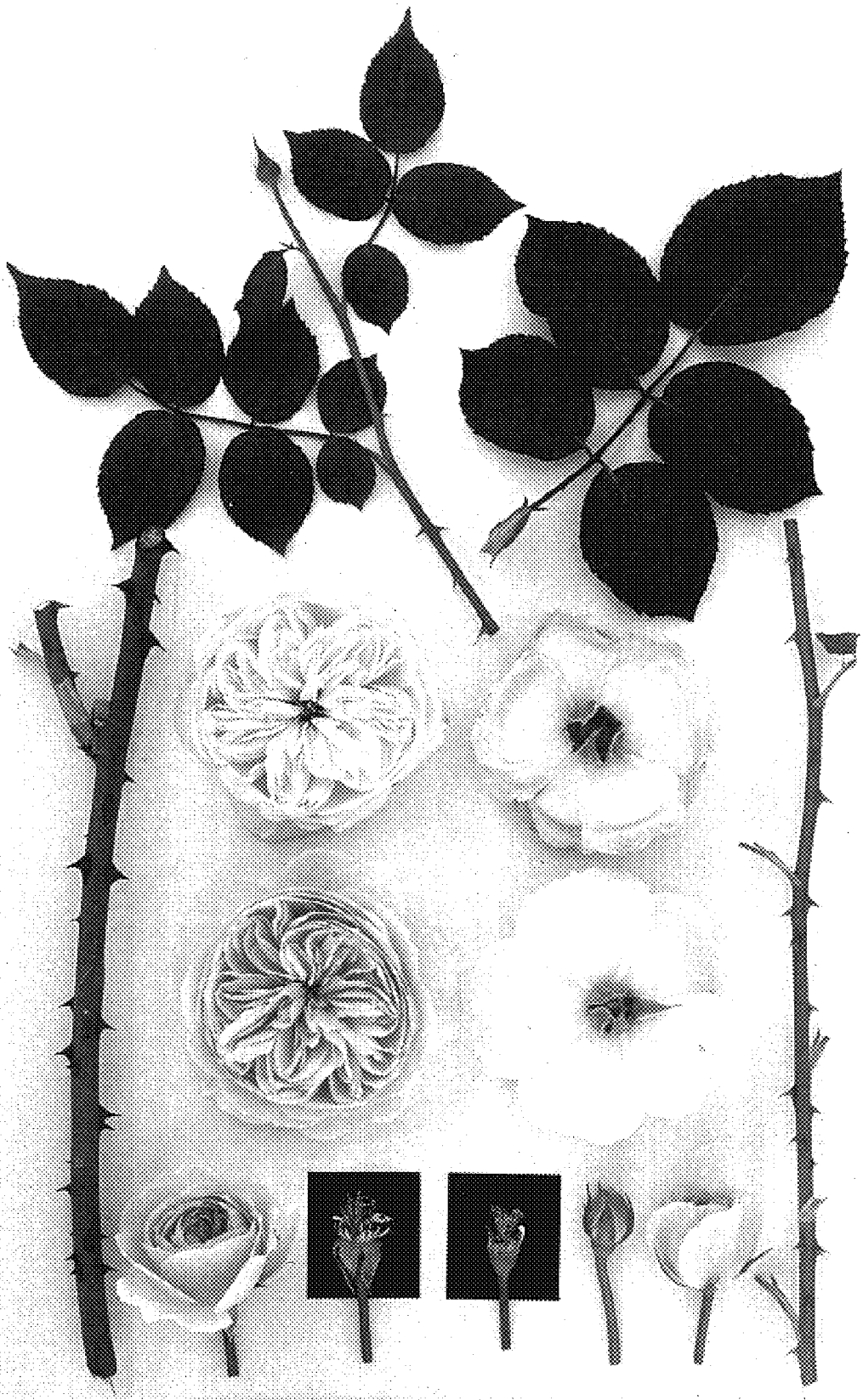
(EUR/PDT/CHT (2)